United States Patent
Yamada et al.

(10) Patent No.: US 11,033,755 B2
(45) Date of Patent: Jun. 15, 2021

(54) TREATMENT PLANNING SYSTEM AND PARTICLE THERAPY SYSTEM

(71) Applicant: Hitachi, Ltd., Tokyo (JP)

(72) Inventors: Takahiro Yamada, Tokyo (JP); Taisuke Takayanagi, Tokyo (JP); Rintarou Fujimoto, Tokyo (JP); Shinichiro Fujitaka, Tokyo (JP); Takuya Nomura, Tokyo (JP)

(73) Assignee: HITACHI, LTD., Tokyo (JP)

( * ) Notice: Subject to any disclaimer, the term of this patent is extended or adjusted under 35 U.S.C. 154(b) by 540 days.

(21) Appl. No.: 15/821,889

(22) Filed: Nov. 24, 2017

(65) Prior Publication Data

US 2018/0200534 A1   Jul. 19, 2018

(30) Foreign Application Priority Data

Jan. 19, 2017  (JP) .............................. JP2017-007164

(51) Int. Cl.
*A61N 5/10*   (2006.01)

(52) U.S. Cl.
CPC .......... *A61N 5/103* (2013.01); *A61N 5/1043* (2013.01); *A61N 5/1071* (2013.01); *A61N 5/1077* (2013.01); *A61N 5/1067* (2013.01); *A61N 2005/1074* (2013.01); *A61N 2005/1087* (2013.01)

(58) Field of Classification Search
CPC ............ A61N 2005/1087; A61N 5/103; A61N 5/1043; A61N 5/1071; A61N 5/1077
See application file for complete search history.

(56) References Cited

U.S. PATENT DOCUMENTS

| 2012/0187314 A1 | 7/2012 | Bert et al. |
| 2014/0206923 A1* | 7/2014 | Hirayama ............ A61N 5/1031 600/1 |
| 2015/0099917 A1* | 4/2015 | Bula .................... A61N 5/1067 600/1 |

FOREIGN PATENT DOCUMENTS

| JP | 4877784 B2 | 2/2012 |
| JP | 2012-532712 A | 12/2012 |
| WO | 2015/145705 A1 | 10/2015 |

OTHER PUBLICATIONS

Japanese Office Action received in corresponding Japanese Application No. 2017-007164 dated Jul. 7, 2020.

* cited by examiner

*Primary Examiner* — Christine H Matthews
(74) *Attorney, Agent, or Firm* — Mattingly & Malur, PC

(57) ABSTRACT

There is provided a treatment planning system and a particle therapy system. In the related art, it is unable to determine optimum beam intensity in irradiation for which discrete spot irradiation and continuous beam irradiation coexist. There is provided a treatment planning system that includes a spot determination unit that divides an irradiation region to be irradiated with a charged particle beam into a plurality of layers in an advancing direction of the charged particle beam and disposes a plurality of irradiation spots, which becomes irradiation points of the charged particle beam, in the layers and a beam intensity determination unit that determines beam intensity for each of the layers by evaluating the irradiation time by changing the beam intensity in a range of a condition of change in dose distribution which is set in advance.

12 Claims, 12 Drawing Sheets

[Fig. 1]
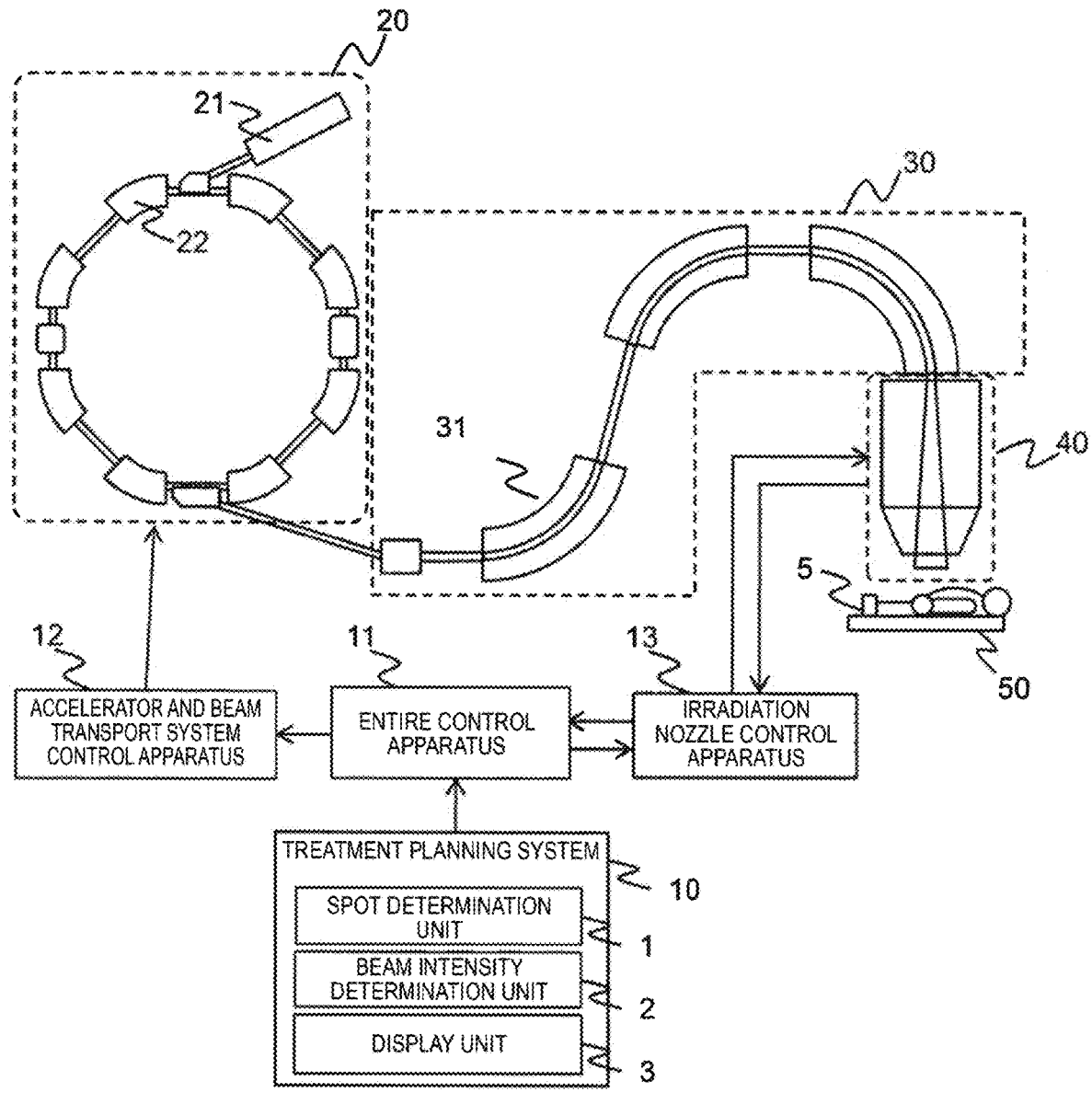

[Fig. 2]
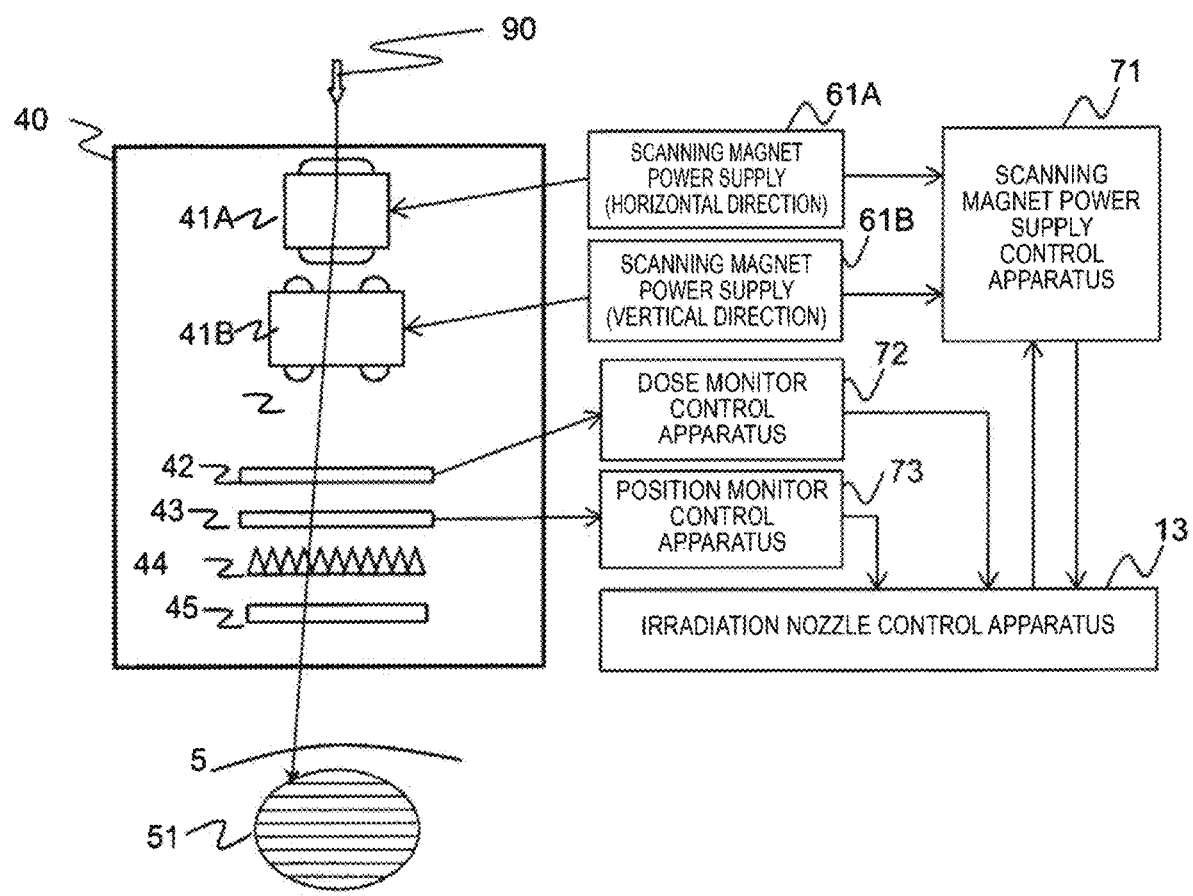

[Fig. 3]
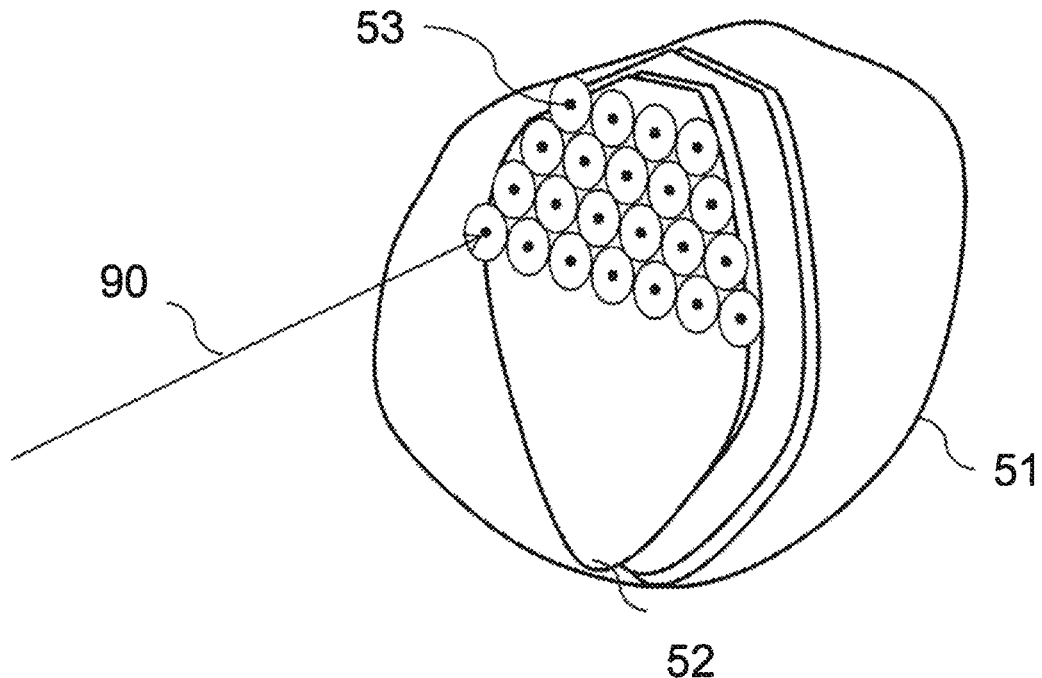
[Fig. 4]
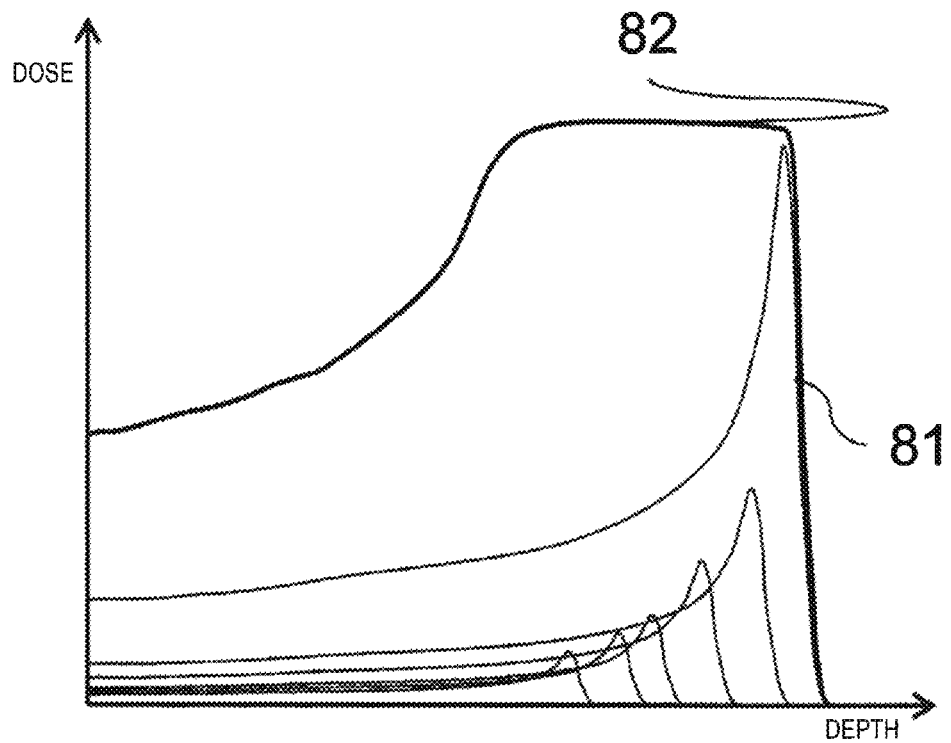

[Fig. 5]
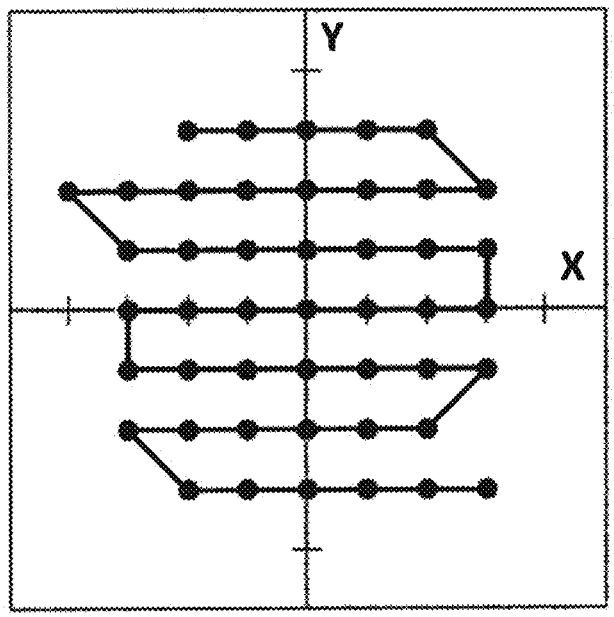
[Fig. 6]
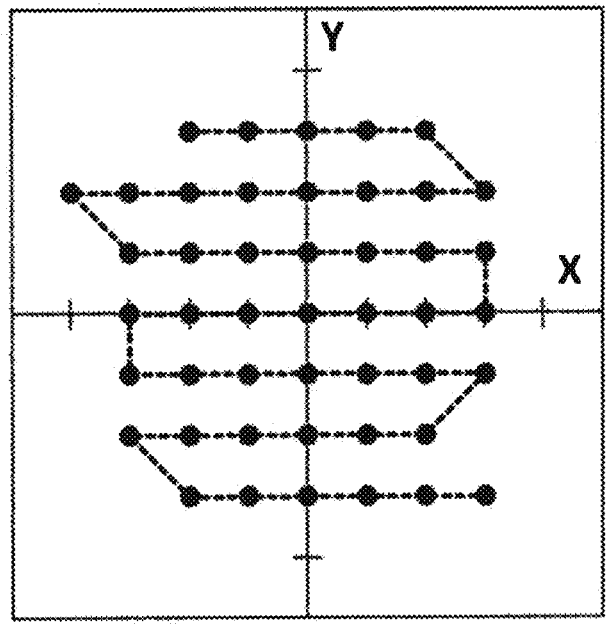

[Fig. 7]
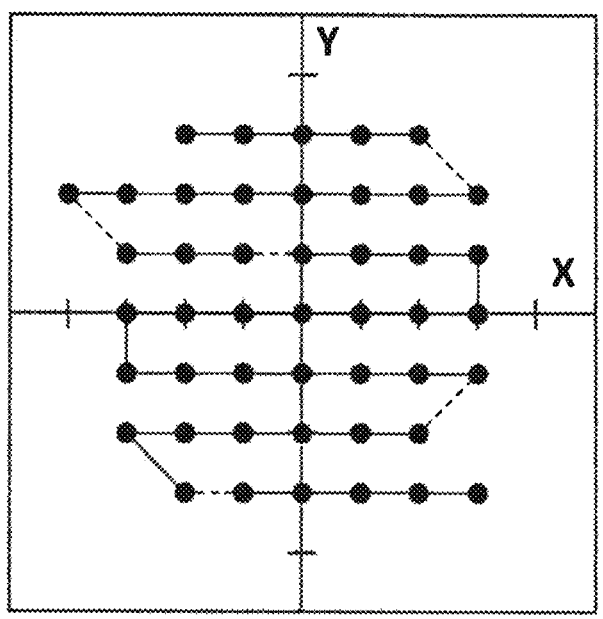

[Fig. 8]
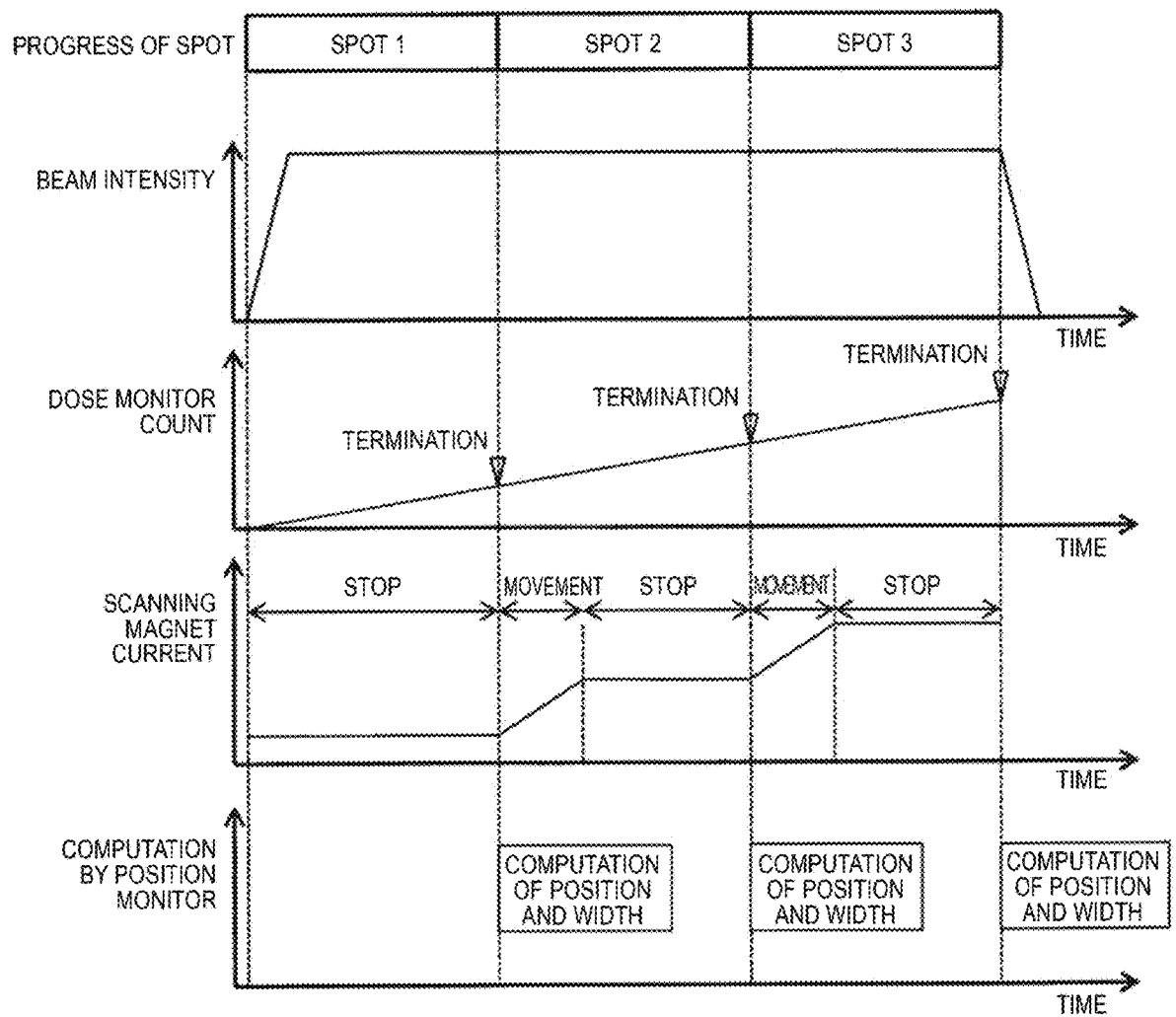

[Fig. 9]
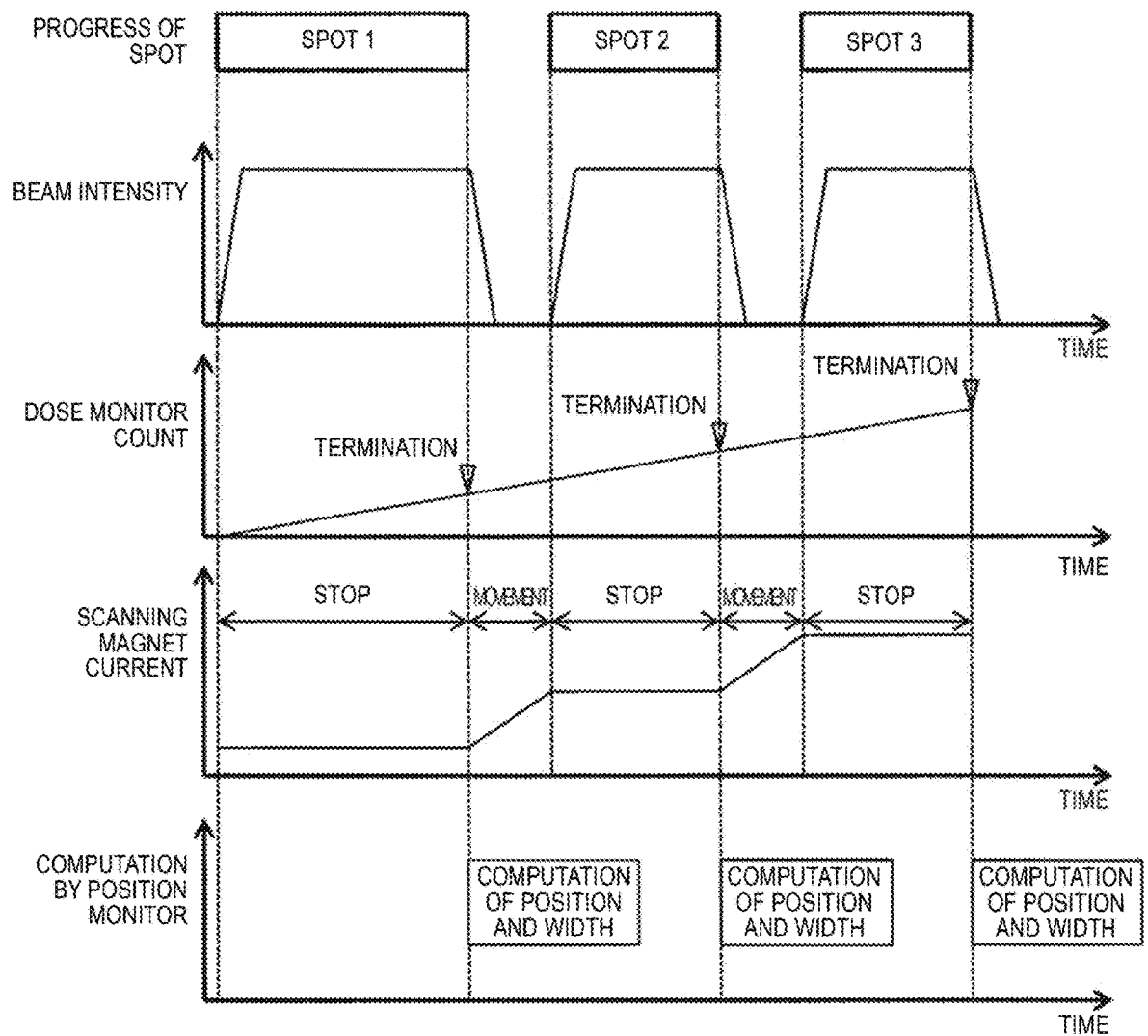

[Fig. 10]
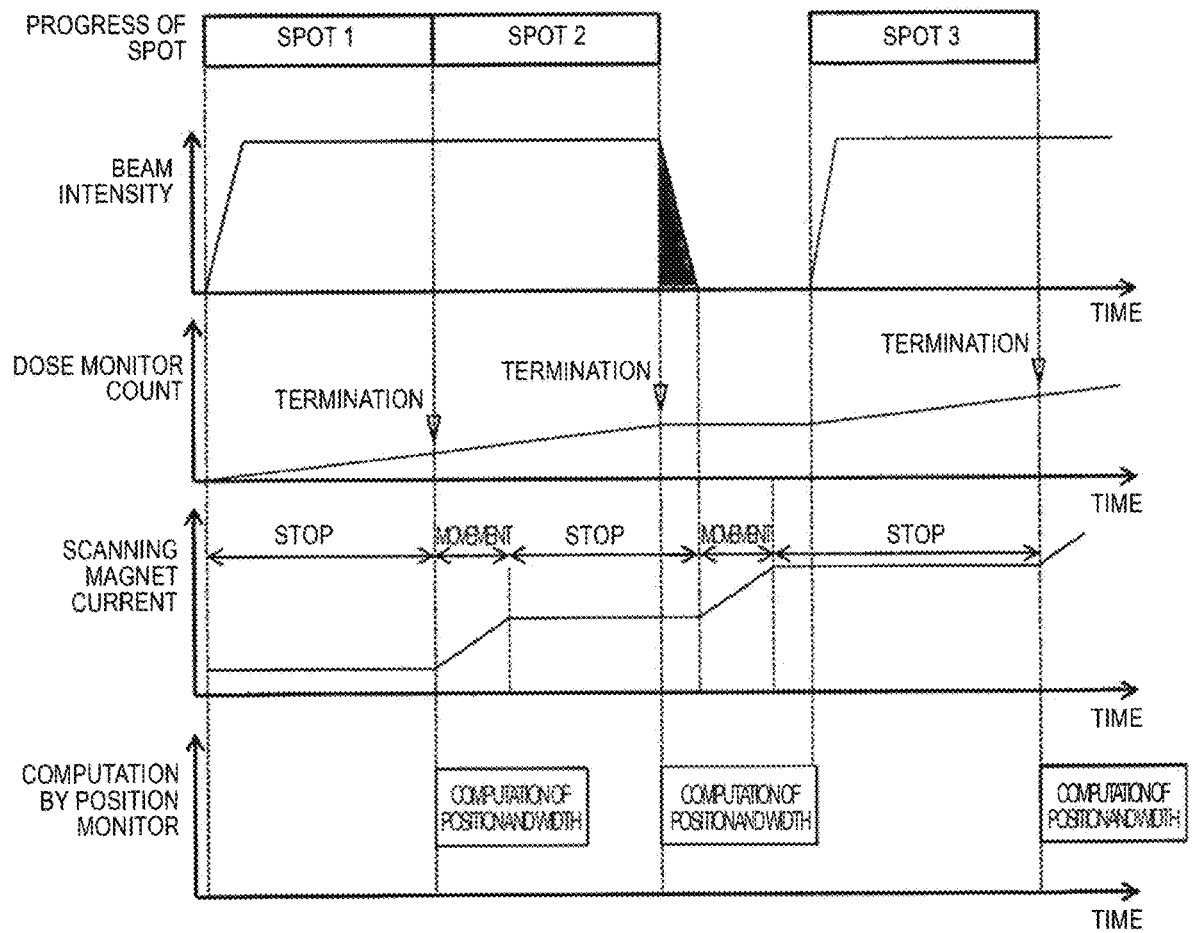

[Fig. 11]
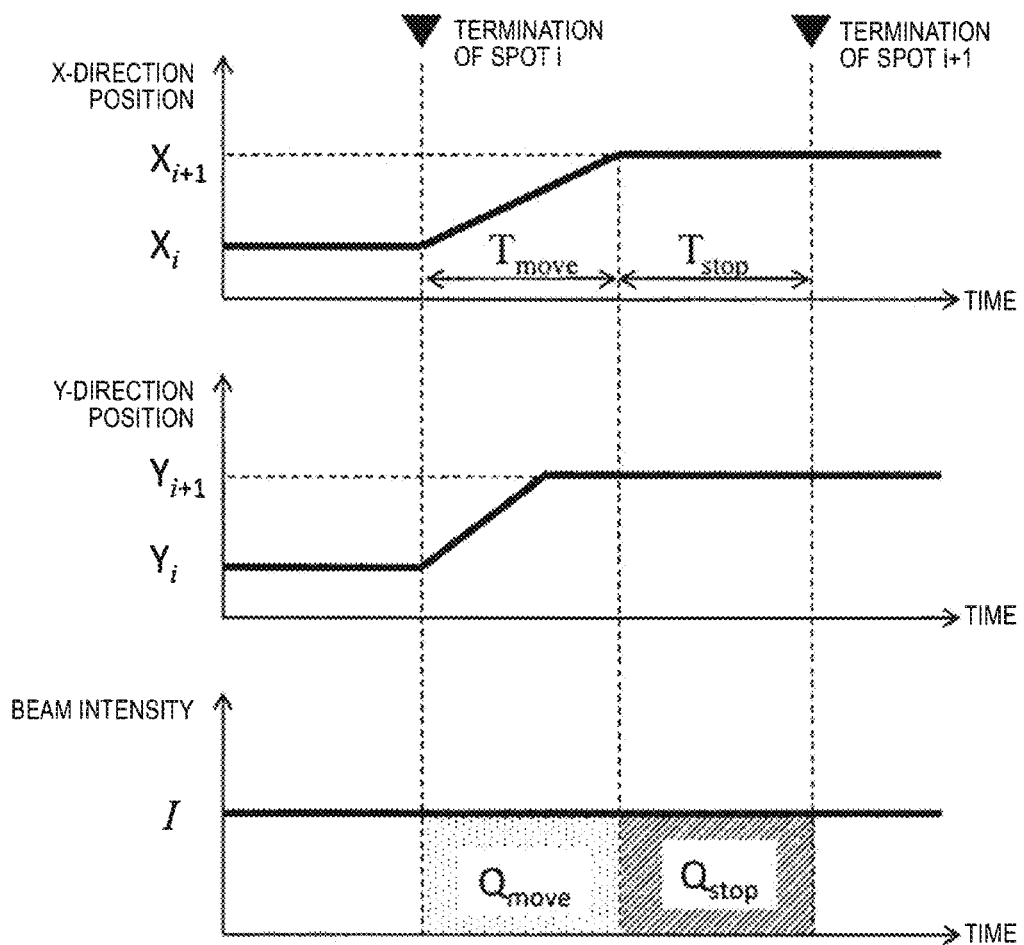

[Fig. 12]
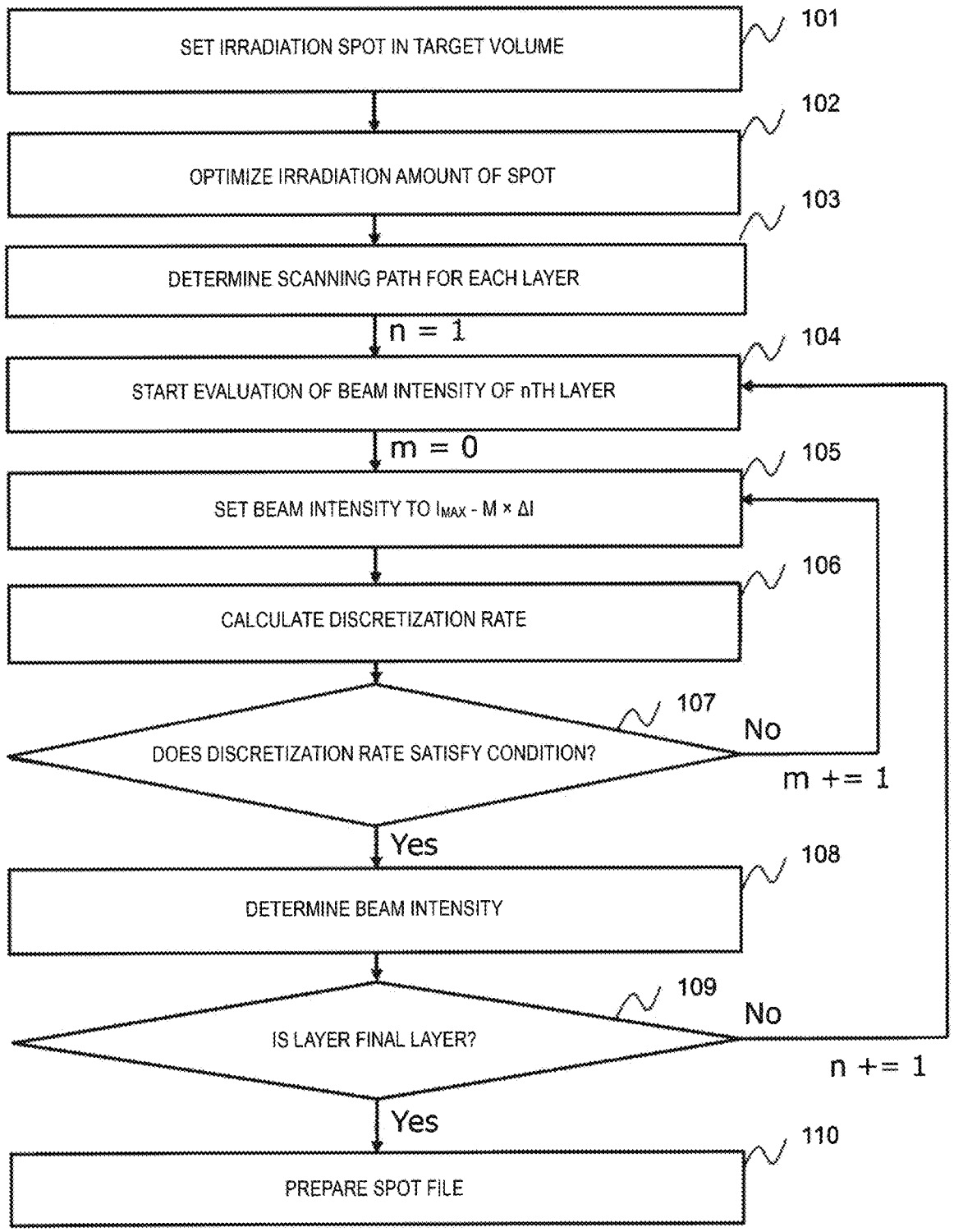

[Fig. 13]
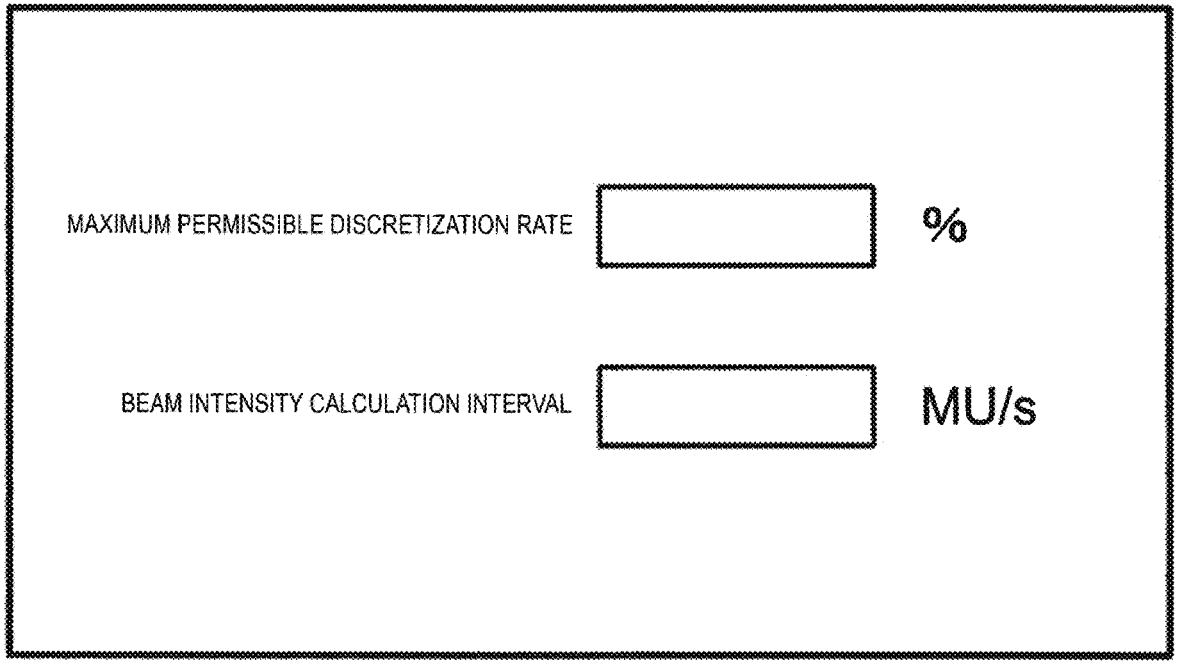
[Fig. 14]
| No. | ENERGY | X | Y | IRRADIATION AMOUNT | BEAM INTENSITY | DISCRETIZATION FLAG |
|---|---|---|---|---|---|---|
| 1 | 220.0 | 1.0 | 1.0 | 0.03 | 5.0 | 0 |
| 2 | 220.0 | 1.5 | 1.0 | 0.03 | 5.0 | 0 |
| 3 | 220.0 | 2.0 | 1.0 | 0.003 | 5.0 | 1 |
| ... | ... | ... | ... | ... | ... | ... |

[Fig. 15]
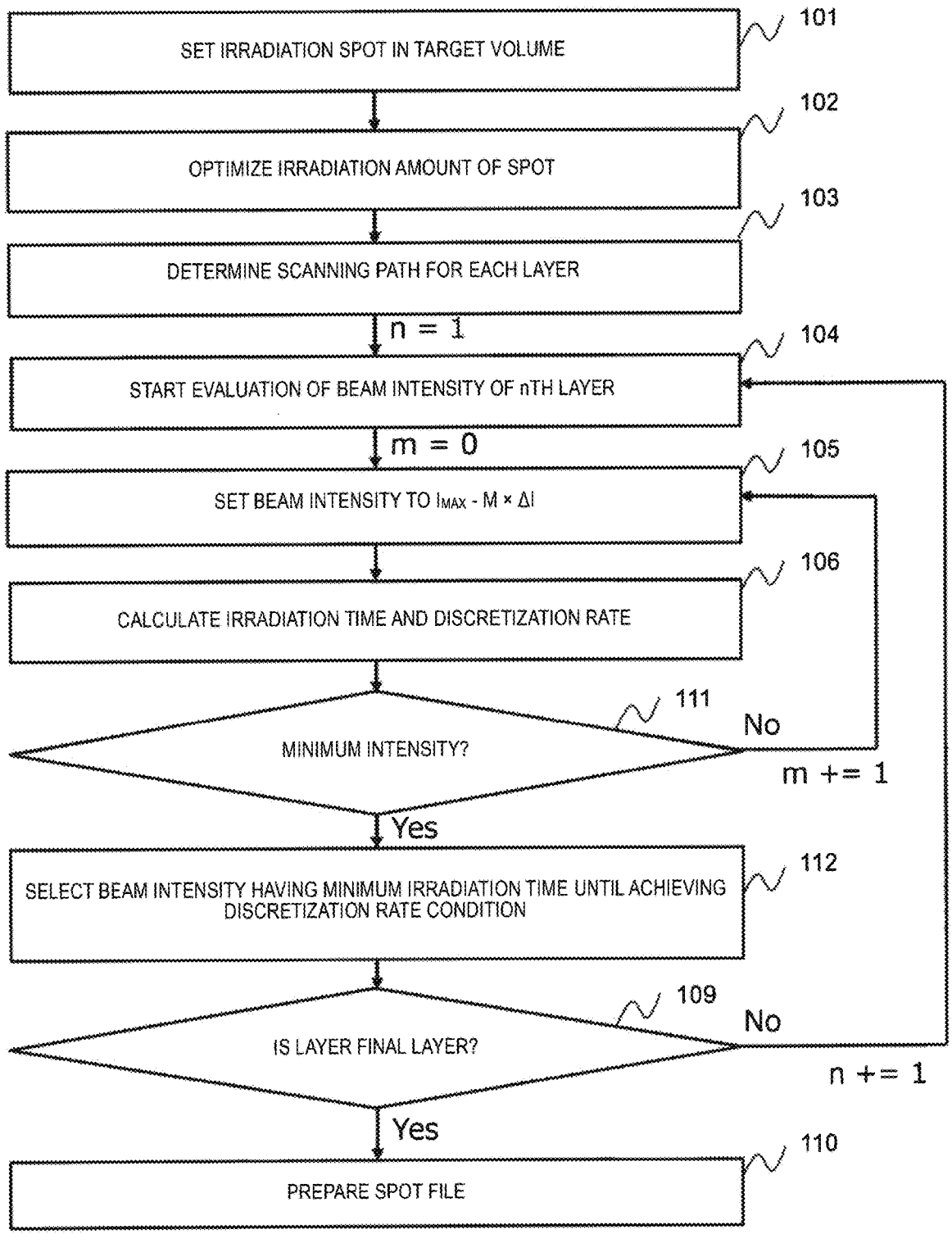

TREATMENT PLANNING SYSTEM AND PARTICLE THERAPY SYSTEM

TECHNICAL FIELD

The present invention relates to a particle therapy system which performs cancer treatment by irradiating tumor volume with a charged particle beam accelerated by a particle accelerator such as a synchrotron or a cyclotron.

BACKGROUND ART

As a method for irradiating the target volume with the charged particle beam in the particle therapy, scanning irradiation which irradiates an irradiation target while directly scanning a beam of charged particles is known. As particle scanning irradiation, there are a plurality of scanning methods for irradiating target volume with a uniform dose. In the scanning irradiation method called discrete spot irradiation, an irradiation spot to be irradiated with a beam on the target volume is disposed and a target irradiation dose of each irradiation spot is determined by a treatment planning system. During irradiation, an irradiation point of the charged particle beam and an irradiation amount thereof are measured and a determined irradiation spot is irradiated with the beam by a predetermined irradiation amount. When beam irradiation for a single irradiation spot is completed, irradiation of the beam is stopped (off) once and movement to a next irradiation spot is performed to turn on the beam again to irradiate the next irradiation spot. Matters described above are repeated for all irradiation spots and irradiation is completed. In energy alteration of the target volume in a depth direction, energy of the charged particle beam is altered by an accelerator to change the irradiation spot in the depth direction.

As another scanning method, there is an irradiation method called continuous beam irradiation, and this method is an irradiation method which is similar to the method for the discrete spot in that when the dose is terminated in the irradiation spot, movement to a next irradiation spot is performed, but movement is performed while irradiation of the beam is performed even during movement between the irradiation spots. In the scanning irradiation by a continuous beam, irradiation planning in which target volume can be irradiated in a uniform dose, after a dose of charged particle beams to be irradiated is also taken into account, needs to be calculated by the treatment planning system.

In PTL 1, a method for determining beam intensity in consideration of dose distribution due to an error of a treatment system in a case of discrete spot irradiation and continuous beam irradiation is disclosed.

CITATION LIST

Patent Literature

PTL 1: Japanese Patent No. 4877784

SUMMARY OF INVENTION

Technical Problem

In the technology described in PTL 1, although the beam intensity can be determined in a case of discrete spot irradiation or continuous beam irradiation, the beam intensity cannot be determined in irradiation in which discrete spot irradiation and continuous beam irradiation coexist.

In a case where a remote spot exists or in a case where spots of a small dose are continuous, there may be a case where coexistence of discrete spot irradiation and continuous beam irradiation is preferable due to limitation on suppression of deterioration in dose distribution and control of the treatment system.

There is a possibility that a delay dose generated at the time of discretization in which switching from continuous beam irradiation to discrete spot irradiation is performed deteriorates dose distribution. When the beam intensity is lowered, influence thereof can be reduced and thus, when the beam intensity is reduced in order to improve dose distribution by reducing the number of discretized spots, irradiation time is increased. On the other hand, in a case where the beam intensity is large, although the irradiation time can be reduced, the number of discretized spots is increased and thus, dose distribution is likely to be deteriorated. As such, in a case where the irradiation time and the dose distribution are in a relationship of trade-off, a method for determining beam intensity is needed.

Solution to Problem

In order to solve the problems to be solved described above, for example, a configuration described in the claims is adopted.

According to the present invention, there is provided a treatment planning system that includes a spot determination unit that divides an irradiation region to be irradiated with a charged particle beam into a plurality of layers in an advancing direction of the charged particle beam and disposes a plurality of irradiation spots, which becomes irradiation points of the charged particle beam, in the layers, and a beam intensity determination unit that evaluates the irradiation time by changing beam intensity in a range of a condition for change in dose distribution which is set in advance and determines beam intensity for each layer.

Advantageous Effects of Invention

According to the present invention, in particle scanning irradiation in which discrete spot irradiation and continuous beam irradiation coexist, suppression of deterioration in dose distribution and reduction of the irradiation time becomes possible.

BRIEF DESCRIPTION OF DRAWINGS

FIG. 1 is a diagram illustrating the entire configuration of a particle therapy system.

FIG. 2 is a diagram illustrating a particle scanning irradiation nozzle.

FIG. 3 is a diagram illustrating layers to be irradiated with the same energy, a charged particle beam, and an irradiation spot when scanning irradiation is performed on target volume.

FIG. 4 is a diagram illustrating dose distribution in a depth direction when scanning irradiation is performed on target volume.

FIG. 5 is a diagram illustrating continuous beam irradiation.

FIG. 6 is a diagram illustrating discrete spot irradiation.

FIG. 7 is a diagram illustrating scanning irradiation in which continuous beam irradiation and discrete spot irradiation coexist.

FIG. 8 is a diagram illustrating control of continuous beam irradiation.

FIG. 9 is a diagram illustrating control of discrete spot irradiation.

FIG. 10 is a diagram illustrating control of scanning irradiation in which continuous beam irradiation and discrete spot irradiation coexist.

FIG. 11 is a diagram for explaining a condition of discretization.

FIG. 12 is a flowchart illustrating a first example of the present invention.

FIG. 13 is a diagram illustrating an example of an input screen of a display unit 3.

FIG. 14 is a diagram illustrating a spot file.

FIG. 15 is a flowchart illustrating a second example of the present invention.

DESCRIPTION OF EMBODIMENTS

Embodiment 1

Specific embodiments in which the present invention is embodied will be described in detail using the accompanying drawings.

FIG. 1 is a diagram illustrating the entire configuration of a particle therapy system which is an embodiment of the present invention. The particle therapy system includes an accelerator 20 accelerating a charged particle beam (in the following, beam) 90, a beam transport system 30 transporting the accelerated beam 90 to an irradiation nozzle, an irradiation nozzle 40 irradiating target volume with the beam, a treatment table 50, a treatment planning system 10 preparing treatment planning, an entire control apparatus 11, an accelerator and beam transport system control apparatus 12, and an irradiation nozzle control apparatus 13. The treatment planning system 10 includes a spot determination unit 1, a beam intensity determination unit 2, and a display unit 3. The accelerator 20 includes an injector 21 and a synchrotron accelerator 22. The beam 90 accelerated up to 60 percent to 70 percent of the velocity of light by the accelerator 20 is transported to the irradiation nozzle 40 while being bent by a magnetic field in a vacuum by a bending magnet 31 disposed in the beam transport system 30. The beam 90 is shaped to be matched with a shape of the irradiation region in the irradiation nozzle 40 and an irradiation target is irradiated with the beam 90. The irradiation target is, for example, target volume 51 of a patient 5 lying down on the treatment table 50.

FIG. 2 is a diagram illustrating the irradiation nozzle 40 for particle scanning which is an embodiment of the present invention. The irradiation nozzle 40 scans the beam 90 within a two-dimensional plane by scanning magnets 41A and 41B for a horizontal direction and a vertical direction. A target volume 51 is irradiated with the beam 90 scanned by the scanning magnets 41A and 41B. A dose monitor 42 measures an irradiation amount of the beam 90 with which each irradiation spot is irradiated. A dose monitor control apparatus 72 controls an irradiation amount for irradiation of each irradiation spot. A position monitor 43 measures the beam position (for example, the center of gravity) of each irradiation spot. A position monitor control apparatus 73 performs a computation of a position and a width of the irradiation spot based on data of the beam position measured by the position monitor 43 and confirms an irradiation point of the beam 90. A ridge filter 44 is used in a case where it is needed to spread out the Bragg peak. A range shifter 45 may be inserted to adjust an arrival position of the beam 90.

In scanning irradiation, a position of an irradiation spot for irradiating target volume with a uniform dose and a target irradiation dose for each irradiation spot are calculated in the treatment planning system 10 illustrated in FIG. 1 in advance. Particle scanning irradiation is illustrated in FIG. 3. The target volume 51 is divided into layers 52 and inside of each layer 52 is irradiated with the beam 90 having the same energy. Irradiation spots 53 are disposed inside each layer 52.

Data for each patient calculated in the treatment planning system 10 illustrated in FIG. 1 is sent to the entire control apparatus 11 of the particle therapy system illustrated in FIG. 1. An energy alteration signal, a beam extraction signal, a beam extraction stop signal, or the like is output from the entire control apparatus 11 to the accelerator and beam transport system control apparatus 12. A coordinate value and an irradiation amount for each irradiation spot are sent from the entire control apparatus 11 to the irradiation nozzle control apparatus 13. A coordinate value of the irradiation spot is converted into an excitation current value of the scanning magnets 41A and 41B and is sent to the scanning magnet power supply control apparatus 71 illustrated in FIG. 2.

When the irradiation spot 53 disposed in the treatment planning system is irradiated with the beam 90 of a fixed irradiation amount, a next irradiation spot 53 is irradiated with the beam 90. When irradiation for a certain layer 52 is completed, irradiation for a next layer 52 is performed. First, change of an irradiation point in an advancing direction of a beam, that is, a target volume depth direction alters energy of a beam. When the energy of the beam is altered, an arrival position in the body of the beam is changed. A charged particle beam having high energy arrives at a deep position in the body and a charged particle beam having low energy arrives at only a shallow position in the body. In particle scanning irradiation, the energy of the beam is altered and the irradiation amount is appropriately distributed in forming uniform dose distribution in the depth direction to form the spread out Bragg peak (SOBP) in the depth direction. Respective irradiation amounts of energy are appropriately to overlap the Bragg curves 81 of energy each other to form dose distribution SOBP 82 which is uniform in the depth direction as illustrated in FIG. 4.

Next, irradiation in the lateral direction of scanning irradiation will be described. In the treatment planning system 10, the irradiation spot for irradiating target volume with a uniform dose is disposed for each beam energy as illustrated in FIG. 3. FIG. 5 illustrates scanning irradiation by continuous beam irradiation, FIG. 6 illustrates scanning irradiation by discrete spot irradiation, and FIG. 7 illustrates scanning irradiation in which the continuous beam irradiation and the discrete spot irradiation coexist (in the following, referred to as combined irradiation). The black dot represents an irradiation spot and the solid line represents irradiation in which the beam is moved between the irradiation spots while turning on the beam, and the dotted line represents irradiation in which the beam is turned off and is moved between the irradiation spots. As illustrated in FIG. 5, in continuous beam irradiation, when the beam is stopped after by an irradiation amount of each irradiation spot determined in treatment planning, the beam is moved to a next irradiation spot without being turned off. For that reason, an irradiation amount of an irradiation spot becomes a sum of an irradiation amount to be irradiated during movement between the irradiation spots and an irradiation amount to be irradiated while being stopped at the irradiation spot. In treatment planning in association with continuous beam irradiation, as illustrated in the solid line of FIG. 5, a scanning path for scanning irradiation spots is determined in advance.

Although discrete spot irradiation illustrated in FIG. 6 illustrates the same scanning path as continuous beam irradiation of FIG. 5, when the irradiation spot is moved, the beam is turned off and movement to the next irradiation spot is performed. For that reason, the dose is given only to the spot illustrated by the black dot illustrated in FIG. 6. As illustrated in FIG. 7, in combined irradiation, although movement to the next irradiation spot is performed without stopping irradiation of the beam in the scanning path illustrated by the solid line, movement to the next irradiation spot is performed after beam irradiation is stopped in the scanning path illustrated by the dotted line. In the following description, a method that beam irradiation is stopped the continuous beam and movement to a next spot is performed is called discretization.

In continuous beam irradiation, movement between the irradiation spots is performed while turning on the beam even between the irradiation spots and thus, irradiation planning is needed by which target volume is irradiated with a uniform dose in consideration of the dose to be irradiated even during movement between spots. For example, a method in which a virtual irradiation spot is disposed between the irradiation spots, a dose of the beam which is being moved is taken as a representative of the dose, and determines the dose by optimization may be adopted. In continuous beam irradiation, the dose of the beam irradiated during movement between the irradiation spots is taken into account and thus, a scanning path in which the irradiation spot is scanned within the layer to be irradiated with the same energy needs to be determined. For example, a method for determining the scanning path using a traveling salesman algorithm so as to minimize a scanning distance for irradiating the irradiation spots may be adopted.

Control of continuous beam irradiation, discrete spot irradiation, and scanning irradiation in which the continuous beam irradiation and the discrete spot irradiation coexist will be described in detail. A timing chart of the continuous beam irradiation is illustrated in FIG. 8. In FIG. 8, irradiation of three spots of a spot 1 to a spot 3 is illustrated as an example. In the accelerator 20, an instruction is output from the accelerator and beam transport system control apparatus 12 illustrated in FIG. 1 so as to allow irradiation with predetermined beam intensity. When irradiation of the beam is started, an ionization output of the dose monitor 42 within the irradiation nozzle 40 is subjected to pulse conversion in the dose monitor control apparatus 72 and a pulse count value is started to increase, and when a predetermined irradiation amount is irradiated, the dose monitor control apparatus 72 sends a termination signal to the irradiation nozzle control apparatus 13, and irradiation for the spot is ended. The irradiation nozzle control apparatus 13 having received the termination signal obtains an output signal of the position monitor 43 from the position monitor control apparatus 73, computes a position and a width of the beam, and determines whether a predetermined position is irradiated with the beam. As a result of determination, when deviation in the beam position and the width is large, irradiation of the beam is stopped. The irradiation nozzle control apparatus 13 sends a next spot movement signal to the scanning magnet power supply control apparatus 71 by the termination signal of the dose monitor control apparatus 72 and movement to the next spot is started. When a current value for the next spot is reached, the scanning magnet power supply control apparatus 71 sends a movement completion signal to the irradiation nozzle control apparatus 13. The above is a flow of control of continuous beam irradiation.

Next, a timing chart of discrete spot irradiation is illustrated in FIG. 9. In discrete spot irradiation, the dose termination signal is received, a scanning magnet current is changed, and movement to a next spot is performed, as in the continuous beam irradiation. In discrete spot irradiation, when the dose termination signal from the dose monitor control apparatus 72 is received, the irradiation nozzle control apparatus 13 sends a beam off instruction to the accelerator and beam transport system control apparatus 12 through the entire control apparatus 11, and the beam is turned off. Thereafter, the accelerator and beam transport system control apparatus 12 sends a movement start signal to the irradiation nozzle control apparatus 13 through the entire control apparatus 11 after turning off of the beam is completed. The irradiation nozzle control apparatus 13 receives the movement start signal and sends a signal of movement to the next spot to the scanning magnet power supply control apparatus 71. When the movement completion signals of the scanning magnet power supplies 61A and 61B are received, a beam on instruction is sent to the accelerator and beam transport system control apparatus 12 so that irradiation of a beam is started again and irradiation for the next spot is started. The irradiation nozzle control apparatus 13 having received the termination signal starts computation of the beam position and the width. A beam is turned off between spots so that a component delayed from a response time of the accelerator 20 exists in the irradiation amount and with this, the irradiation amount of each spot is increased by an amount of the delay component. For that reason, in discrete spot irradiation, accuracy of the irradiation amount is secured by integrating all irradiation amounts to be managed regardless of it is during a stop.

Next, a timing chart of combined irradiation is illustrated in FIG. 10. In combined irradiation, the dose termination signal is received, a scanning magnet current is changed, and movement to a next spot is performed, as in the continuous beam irradiation and the discrete spot irradiation. In the accelerator 20, an instruction is output from the accelerator and beam transport system control apparatus 12 illustrated in FIG. 1 so that irradiation with predetermined beam intensity is performed. When irradiation of the beam is started, an ionization output of the dose monitor 42 within the irradiation nozzle 40 is subjected to pulse conversion in the dose monitor control apparatus 72 and a pulse count value is started to increase, and when a predetermined irradiation amount is irradiated, the dose monitor control apparatus 72 sends a termination signal to the irradiation nozzle control apparatus 13, and irradiation for the spot is ended. In a case where the next spot is irradiated with a continuous beam, the irradiation nozzle control apparatus 13 sends a next spot movement signal to the scanning magnet power supply control apparatus 71 by the termination signal of the dose monitor control apparatus 72 and movement to the next spot is started. In a case where a next spot is irradiated with discrete spot irradiation, the irradiation nozzle control apparatus 13 sends the beam off instruction to the accelerator and beam transport system control apparatus 12 through the entire control apparatus 11 and the beam is turned off. Thereafter, the accelerator and beam transport system control apparatus 12 sends the movement start signal to the irradiation nozzle control apparatus 13 through the entire control apparatus 11 after turning off of the beam is completed. The irradiation nozzle control apparatus 13 receives the movement start signal and sends a signal of movement to a next spot to the scanning magnet power supply control apparatus 71. When the movement completion signals of the scanning magnet power supplies 61A and 61B are received and a beam on instruction is sent to the accelerator and beam transport system control apparatus 12 so that irradiation of a beam is started again and irradiation for the next spot is started. Also, in a case where a next spot is irradiated with one of the continuous beam irradiation and the discrete spot irradiation, the computation of the beam position and the width is started by the termination signal for the irradiation spot. When the beam is turned off due to discretization, a delay dose delayed from the response time of the accelerator 20 exists and with this, the irradiation amount of discrete spot irradiation is increased by an amount of the delay dose. The delay dose is likely to be causes of deterioration of dose distribution.

As described above, although the control methods for respective irradiation are described, beam irradiation is not performed during movement between the irradiation spots while in the continuous beam irradiation, the beam is irradiated even during movement between the irradiation spots and thus, it is possible to shorten treatment time in the continuous beam irradiation than in the discrete spot irradiation. However, all spots cannot be irradiated using continuous beam irradiation and are discretized due to limitation on control.

The condition of discretization will be described using FIG. 11. FIG. 11 illustrates a spot position and beam intensity in an X-direction and a Y-direction. $Q_{move}$, $Q_{top}$, $T_{move}$, and $T_{stop}$ represent an irradiation dose during movement, an irradiation dose during a stop, a movement time, and a stop time, respectively. When scan velocity in the X-direction and scan velocity in the Y-direction are regarded as $V_x$ and $V_y$, the movement time is expressed as the expression (1).

[Expression 1]

$$T_{move} = \max\left(\frac{X_{i+1} - X_i}{V_x}, \frac{Y_{i+1} - Y_i}{V_y}\right) \quad (1)$$

When beam intensity is I, if an irradiation amount of a spot i+1 is regarded as $Q_{i+1}$, the stop time is expressed as the expression (2).

[Expression 2]

$$T_{stop} = \frac{Q_{i+1}}{I} - T_{move} \quad (2)$$

The $Q_{move}$ and $Q_{stop}$ are expressed as the expression (3).

[Expression 3]

$$Q_{move} = I \cdot T_{move}$$

$$Q_{stop} = Q_{i+1} - Q_{move} \quad (3)$$

When an irradiation dose needed to compute the beam position and the width in the position monitor 43 is regarded as $Q_{min}$, a stop dose of a spot which does not satisfy the following expression (4) is small and the beam position and the width cannot be computed for the spot and thus, it is needed to secure an irradiation dose needed for computation of the position and the width by discretizing the spot.

[Expression 4]

$$Q_{stop} \geq Q_{min} \quad (4)$$

Although computation of the beam position and the width is started by the termination signal for the irradiation spot, the irradiation nozzle control apparatus 13 cannot receive the termination signal for a next spot before computation for the previous spot is ended. That is, when the time required for computation of the beam position and the width is regarded as $t_{min}$, the spot which does not satisfy the following expression (5) needs to be discretized and irradiated again after the computation of the position and the width of the previous spot is ended.

[Expression 5]

$$T = \frac{Q_{move} + Q_{stop}}{I} > t_{min} \quad (5)$$

As expressed in the expression (3), the irradiation dose during movement is proportional to the beam intensity in the spot irradiated with the continuous beam. For that reason, in a case where there is an error in beam intensity, the percentage of the irradiation dose during movement and the irradiation dose during a stop are changed from planned one. In a case where the irradiation dose during movement is larger than the irradiation dose during a stop, dose distribution is likely to be deteriorated and thus, limitation may be set on the ratio of the irradiation dose during movement and the irradiation dose during a stop. That is, the spot which does not satisfy the following expression (6) needs to be discretized.

[Expression 6]

$$\frac{Q_{stop}}{Q_{move}} > C \quad (6)$$

Here, C is a limit value of the ratio of the dose during a stop and the dose during movement.

As described above, the spot which does not satisfy the expressions (4) to (6) should be discretized and thus, as a result, it becomes scanning irradiation in which continuous beam irradiation and discrete spot irradiation coexist. All the expressions (4), (5), and (6) depend on beam intensity and thus, the spot discretized by being depended on beam intensity is changed even in disposition of spots located at the same position and having the same dose. In a case where beam intensity is small, the number of spots to be discretized becomes small and the irradiation time increases and in a case where beam intensity is large, the number of spots to be discretized becomes larger and dose distribution is likely to be deteriorated due to the delay dose.

A treatment planning preparation method in the first embodiment will be described using FIG. 12. When irradiation planning of continuous beam irradiation is calculated in the treatment planning system, first, the spot determination unit 1 included in the treatment planning system divides target volume 51 into the layers 52 and sets irradiation spots 53 (Step 101). Next, irradiation amount optimization is conducted by the repetitive calculation of the quasi-Newton method or the like so that the dose of target volume becomes a predetermined dose (Step 102). As a result, a target irradiation amount for each irradiation spot is determined. Next, a scanning path in the layers is determined (Step 103). In scanning path determination, the traveling salesman algorithm or the like is used so as to minimize the total scanning distance. When the scanning path is determined, the beam intensity determination unit 2 starts evaluating beam intensity of a first layer (Step 104). Beam intensity is set to the maximum value $I_{max}$ which can be set (Step 105) and a discretization rate is calculated (Step 106). Here, the discretization rate represents percentage of the discretized spots to all spots within the layers. A permitted maximum discretization rate is set in advance in order to suppress deterioration of dose distribution due to the delay dose. It is determined whether the calculated discretization rate satisfies the condition of discretization or not (Step 107), and in a case where it is determined that the calculated discretization rate does not satisfy the condition, beam intensity which is obtained by making small by the evaluation interval ΔI of the beam intensity, which is set in advance, is set again (Step 105). Beam intensity when the condition of discretization is satisfied is determined as beam intensity of the layer (Step 108). Similarly, after beam intensity is determined for all layers, a spot file is prepared (Step 110). As such, beam intensity is determined so as to make it possible to reduce the irradiation time in a range in which change in dose distribution is permissible.

For example, the discretization rate is percentage of the irradiation spots, for which irradiation of the charged particle beam is stopped when the beam is moved from the previous spot, among the irradiation spots within the layers.

In the above description, although the discretization rate is used as an index of change in dose distribution due to the error dose, as settings of a condition for suppressing change in dose distribution, it is possible to actually calculate change in dose distribution due to the delay dose in Step 106 and to determine change in dose distribution in Step 107. In a case where dose distribution is actually calculated and change in dose distribution is determined, the maximum value or a change width of change in a dose within a target can be used as a determination criteria.

The condition of the discretization rate or the like can be set based on, for example, the irradiation dose needed to compute the beam position or the width in the position monitor, time required for computation of the spot position and the width, or a ratio of the irradiation dose during movement and during a stop, for the above reasons.

In FIG. 13, an example of a screen in which the maximum permissible discretization rate and the beam intensity calculation interval is input using the display unit 3 of the treatment planning system 10 is illustrated. When treatment planning is prepared, an appropriate value is set using the screen.

An example of the spot file is illustrated in FIG. 14. In the spot file, a spot number, beam energy, a spot position (X, Y), a spot irradiation dose, beam intensity, and a discretization flag are listed. The discretization flag indicates a discretized spot and a spot having a value of 0 is irradiated with continuous beam irradiation and a spot having a value of 1 is discretized.

Embodiment 2

A second embodiment of the present invention will be described. In comparison with the first embodiment, the beam intensity determination method of the present embodiment is different from that of the first embodiment.

A treatment planning method of the present embodiment will be described using FIG. 15. The irradiation spot is set and the scanning path is determined for each layer as in the first embodiment. In the present embodiment, beam intensity is changed within a settable range to evaluate the irradiation time and the discretization rate. Thereafter, beam intensity of which the irradiation time becomes the shortest is selected among beam intensities satisfying the condition of the discretization rate (Step 109). By doing as described above, the irradiation time is not simply increased with respect to beam intensity and it becomes possible to select optimum beam intensity even for the spot having a minimum value.

In addition to the synchrotron accelerator 22 described in Examples 1 and 2, a cyclotron accelerator or the like may be used.

REFERENCE SIGNS LIST

1: spot determination unit
2: beam intensity determination unit
3: display unit
5: patient
10: treatment planning system
11: entire control apparatus
12: accelerator and beam transport system control apparatus
13: irradiation nozzle control apparatus
20: accelerator
21: injector
22: synchrotron accelerator
30: beam transport system
31: bending magnet
40: irradiation nozzle
41A and 41B: scanning magnet
42: dose monitor
43: position monitor
44: ridge filter
45: range shifter
50: treatment table
51: target volume
52: layer of target volume to be irradiated with the same energy
53: irradiation spot
55: remote irradiation spot
56-1, 56-2, 56-3: group of irradiation spots
61A and 61B: scanning magnet power supply
71: scanning magnet power supply control apparatus
72: dose monitor control apparatus
73: position monitor control apparatus
81: Bragg curve
82: SOBP (Spread Out Bragg Peak)
90: charged particle beam

The invention claimed is:

1. A treatment planning system comprising:
a controller configured to:
divide an irradiation region to be irradiated with a charged particle beam into a plurality of layers in an advancing direction of the charged particle beam and determine a target irradiation amount for a plurality of irradiation spots within the layers; and
determine beam intensity for each of the layers based on a condition set in advance for suppressing change in dose distribution due to an error dose,
wherein a beam intensity value that satisfies the condition for suppressing change in dose distribution is obtained by decreasing the beam intensity by a predetermined change interval which is set in advance in a descending order from a settable maximum value, or obtained by decreasing the beam intensity by a predetermined change interval and selecting the beam intensity of which an irradiation time becomes a shortest among beam intensities satisfying the condition.

2. The treatment planning system according to claim 1, wherein the condition for suppressing change in dose distribution due to the error dose is set based on percentage of the irradiation spots, for which irradiation of the charged particle beam is stopped when the beam is moved from a previous spot, among irradiation spots within the layers.

3. The treatment planning system according to claim 1, wherein the condition for suppressing change in dose distribution due to the error dose is set based on a maximum value of change in a dose within the layer.

4. The treatment planning system according to claim 1, wherein the controller is further configured to determine beam intensity for each of the layers based on a discretization rate that represents a percentage of discretizing irradiation spots to all irradiation spots within the layers, wherein a maximum permissible discretization rate is set as the condition for suppressing change in dose distribution due to an error dose.

5. The treatment planning system according to claim 4, wherein a beam intensity value that satisfies the discretization rate set for suppressing change in dose distribution due to an error dose is obtained by decreasing the beam intensity by the predetermined change interval which is set in advance in the descending order from the settable maximum value.

6. A particle therapy system comprising:
an accelerator that accelerates a particle;
a beam transport system that transports an accelerated beam;
an irradiation nozzle that performs irradiation with the transported beam; and
a treatment planning system comprising:
a controller configured to:
divide an irradiation region to be irradiated with a charged particle beam into a plurality of layers in an advancing direction of the charged particle beam and determine a target irradiation amount for a plurality of irradiation spots within the layers; and
determine beam intensity for each of the layers based on a condition set in advance for suppressing change in dose distribution due to an error dose,
wherein the condition for suppressing change in dose distribution due to the error dose is set so that an irradiation dose during a stop is greater than an irradiation dose needed to compute a beam position or a width in a position monitor provided in the irradiation nozzle, or is set based on a time needed to compute a spot position and a width in the position monitor provided in the irradiation nozzle, or is set based on a ratio of the irradiation dose during movement and during a stop.

7. A treatment planning system comprising:
a controller configured to:
divide an irradiation region to be irradiated with a charged particle beam into a plurality of layers in an advancing direction of the charged particle beam and further determine a target irradiation amount for a plurality of irradiation spots within the layers to determine an irradiation plan,
wherein the irradiation plan includes a scanning path along which the charged particle beam moves in the layers in which a combination of irradiation with the charged particle beam is not stopped at a time of movement to a first next one of the irradiation spots and in which irradiation with the charged particle beam is stopped at the time of movement to a second next one of the irradiation spots that is different than the first next one of the irradiation spots, and
determine an intensity of the charged particle beam for each of the layers in a range of a condition set in advance for suppressing change in dose distribution due to an error dose.

8. The treatment planning system according to claim 7, wherein the condition for suppressing change in dose distribution due to an error dose is set using percentage of the irradiation spots, for which irradiation of the charged particle beam is stopped when the beam is moved from a previous spot, among irradiation spots within the layers.

9. The treatment planning system according to claim 8, wherein the intensity of the charged particle beam for each layer is determined as intensity of the charged particle beam obtained when the percentage of the irradiation spots, for which irradiation of the charged particle beam is stopped when the beam is moved from the previous spot, among the irradiation spots within the layers satisfies a condition which is set in advance by decreasing the beam intensity by a change interval which is set in advance from a settable maximum value.

10. The treatment planning system according to claim 8, wherein the intensity of the charged particle beam for each of the layers is determined as an intensity of the charged particle beam for which an irradiation time becomes a shortest time among beam intensities for the spots satisfying the condition, by decreasing the beam intensity of the charged particle beam by a change interval which is set in advance, and by calculating a time required for irradiation and the percentage of irradiation spots for which irradiation of the charged particle beam is stopped when the beam is moved from the previous spot, among the irradiation spots within the layers.

11. The treatment planning system according to claim 9, further comprising:
a display unit that sets a maximum permissible value of the percentage of the irradiation spots for which the irradiation of the charged particle beam is stopped when the beam is moved from the previous spot, among the irradiation spots within the layers.

12. A particle therapy system comprising:
an acceleration apparatus that accelerates a charged particle beam;
an irradiation apparatus that extracts a charged particle beam on a plurality of
irradiation spots disposed in layers in which irradiation regions to be irradiated with the charged particle beam are divided in an advancing direction of the charged particle beam;
a control apparatus that controls the acceleration apparatus and the irradiation apparatus; and
a treatment planning system that determines an irradiation plan for irradiating the irradiation spots,
wherein the irradiation plan includes a scanning path along which the charged particle beam moves in the layers in which a combination of irradiation with the charged particle beam is not stopped at a time of movement to a first next one of the irradiation spots and irradiation with the charged particle beam is stopped at the time of movement to a second next one of the irradiation spots that is different than the first next one of the irradiation spots, wherein the treatment planning system determines an irradiation point of the irradiation spot, an irradiation dose of the irradiation spot, and intensity of the charged particle beam, wherein the intensity of the charged particle beam for each of the layers is determined in a range of a condition set in advance for suppressing change in dose distribution due to an error dose, and wherein the condition for suppressing change in dose distribution due to the error dose is set so that an irradiation dose during a stop is greater than an irradiation dose needed to compute a beam position or a width in a position monitor provided in an irradiation nozzle, or is set based on a time needed to compute a spot position and a width in the position monitor provided in the irradiation nozzle, or is set based on a ratio of the irradiation dose during movement and during a stop.

* * * * *